(12) United States Patent
Moreo et al.

(10) Patent No.: US 11,027,972 B2
(45) Date of Patent: Jun. 8, 2021

(54) PROCESS COMPRISING EXOTHERMAL CATALYTIC REACTION OF A SYNTHESIS GAS AND RELATED PLANT

(71) Applicant: CASALE SA, Lugano (CH)

(72) Inventors: Pietro Moreo, Lugano (CH); Fabio Sassi, Vedano Olona (IT)

(73) Assignee: CASALE SA, Lugano (CH)

( * ) Notice: Subject to any disclaimer, the term of this patent is extended or adjusted under 35 U.S.C. 154(b) by 0 days.

(21) Appl. No.: 16/482,553

(22) PCT Filed: Jan. 31, 2018

(86) PCT No.: PCT/EP2018/052348
§ 371 (c)(1),
(2) Date: Jul. 31, 2019

(87) PCT Pub. No.: WO2018/149638
PCT Pub. Date: Aug. 23, 2018

(65) Prior Publication Data
US 2020/0031664 A1    Jan. 30, 2020

(30) Foreign Application Priority Data
Feb. 14, 2017   (EP) .................................... 17156052

(51) Int. Cl.
*C01B 3/38*       (2006.01)
*B01J 19/00*      (2006.01)
(Continued)

(52) U.S. Cl.
CPC ........... *C01B 3/388* (2013.01); *B01J 19/0013* (2013.01); *B01J 19/245* (2013.01);
(Continued)

(58) Field of Classification Search
CPC ............ C01B 3/382; C01B 2203/1241; C01B 2203/0233; C01B 2203/062; C01B 2203/061; C07C 29/1518
See application file for complete search history.

(56) References Cited

U.S. PATENT DOCUMENTS 5,324,452 A    6/1994  Allam et al.
6,387,963 B1   5/2002  Fitzpatrick
(Continued)

FOREIGN PATENT DOCUMENTS

GB         2066841 A      7/1981

OTHER PUBLICATIONS

International Preliminary Report on Patentability for International Application No. PCT/EP2018/052348 completed Jun. 3, 2019.
(Continued)

*Primary Examiner* — Jafar F Parsa

(57) ABSTRACT

A synthesis process comprising steam reforming a gaseous hydrocarbon feedstock; exothermically reacting the resulting synthesis gas; removing heat from said exothermal reaction by producing steam; using said steam as heat input to the steam reforming, wherein the steam reforming comprises: a) forming a mixture containing steam and hydrocarbons by at least the step of adding a first stream of water to the hydrocarbon feedstock; b) heating said mixture by indirect heat exchange with synthesis gas; c) reforming said mixture after said heating step b).

9 Claims, 2 Drawing Sheets

(51) Int. Cl.
*B01J 19/24* (2006.01)
*C07C 29/151* (2006.01)

(52) U.S. Cl.
CPC . *C07C 29/1518* (2013.01); *B01J 2219/00024* (2013.01); *B01J 2219/00092* (2013.01); *B01J 2219/00128* (2013.01); *C01B 2203/0233* (2013.01); *C01B 2203/061* (2013.01); *C01B 2203/0844* (2013.01); *C01B 2203/0894* (2013.01); *C01B 2203/1276* (2013.01); *C01B 2203/1294* (2013.01)

(56) References Cited

U.S. PATENT DOCUMENTS 7,144,923 B2 * 12/2006 Fitzpatrick ............ C07C 29/152
518/706
2003/0022948 A1 1/2003 Seiki et al.

OTHER PUBLICATIONS

International Search Report from International Application No. PCT/EP2018/052348 dated May 25, 2018.

* cited by examiner

PROCESS COMPRISING EXOTHERMAL CATALYTIC REACTION OF A SYNTHESIS GAS AND RELATED PLANT

FIELD OF APPLICATION

The present invention relates to a process comprising an exothermal catalytic reaction of a synthesis gas and a related plant. The process of the invention applies in particular to the synthesis of methanol.

PRIOR ART

A synthesis process of the type considered herein comprises: steam reforming a gaseous hydrocarbon feedstock in a front-end section, obtaining a synthesis gas; exothermically reacting the resulting synthesis gas in the presence of a catalyst in a synthesis section, obtaining a synthesis product; removing heat from the synthesis section by producing steam; using said steam as heat input to the steam reforming process. A noticeable example of such a process is the synthesis of methanol.

A problem of this type of processes is the strong dependence of the front-end section on the synthesis section, which means that in case of shut-down of the synthesis section, also the front-end section might have to be shut down. This constitutes a significant drawback, because the front-end section has a start-up time which is much longer than the synthesis section. Hence, any undesired shut-down of the front-end section should be avoided.

Reference is made below to a process for the synthesis of methanol, which is taken as a non-limiting example.

A process for the synthesis of methanol basically comprises the production of a make-up synthesis gas by reforming of a hydrocarbon feedstock such as natural gas in a front-end section, and the conversion of said make-up synthesis gas into methanol in a synthesis section.

Said make-up synthesis gas is typically a mixture of carbon oxides and hydrogen with a molar ratio $(H_2-CO_2)/(CO+CO_2)$ of 2.

The front-end section typically includes a saturating tower, wherein the hydrocarbon feedstock is contacted with water, and a reforming section at least comprising a steam reformer, wherein the so obtained water-saturated hydrocarbon feedstock is reformed.

The make-up synthesis gas is obtained at a pressure of about 50 bar which is lower than the synthesis pressure, and is elevated to the synthesis pressure of about 80-150 bar in a suitable gas compressor upstream the synthesis section.

The conversion of the make-up synthesis gas into methanol involves the following reactions of hydrogenation of carbon oxides (CO, $CO_2$) and reversed water-gas shift reactions:

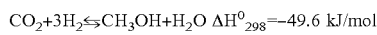

The global process is exothermic and is typically performed in an isothermal converter, which enables heat recovery with production of steam at about 30 bar.

The main share (typically higher than 94%) of the steam produced in the synthesis section is used to supply heat to the water circulating in the saturating tower, thus contributing to provide about 70% of the process steam required in the front-end section. As a result, the saturating tower assures the main portion of steam necessary for a safe and efficient steam reforming.

An important parameter governing the process is the steam-to-carbon ratio, also referred to as SC ratio. The steam-to-carbon ratio is the molar ratio between water (steam) admitted to the process and the carbon contained in the hydrocarbon feedstock. If the SC ratio drops below a certain value, the reforming section is automatically shut down. The lower limit of SC ratio is generally comprised in the range 1.6-1.7.

Although using the steam produced in the synthesis section to supply heat in the saturation tower allows an efficient use of the heat available in the plant, it strongly binds the synthesis section with the front-end section with the disadvantages already mentioned above.

A prior art solution to this problem is to provide steam to the front-end section either by a boiler or the steam network. However, this solution is not practical, since it is difficult to quickly increase the boiler duty and to have much flexibility on the steam network.

GB 2 066 841 discloses a method of producing synthesis gas from steam and a hydrocarbon feed by reformation, which method comprises contacting the hydrocarbon feed directly with water prior to reformation.

U.S. Pat. No. 6,387,963 discloses methanol synthesis including saturation with water of a hydrocarbon feedstock from which the make-up gas is produced by steam reforming.

SUMMARY OF THE INVENTION

The aim of the invention is to provide a synthesis process of the type considered herein, wherein the front-end section is less dependent on the synthesis section.

This aim is reached with a synthesis process according to claim 1, which comprises:
steam reforming a gaseous hydrocarbon feedstock obtaining a synthesis gas;
exothermically reacting said synthesis gas in the presence of a catalyst, obtaining a synthesis product;
removing heat from said exothermal reaction by producing steam,
wherein at least part of said steam provides a heat input to the reforming of said hydrocarbon feedstock;
characterized in that the steam reforming of the hydrocarbon feedstock comprises:
a) forming a mixture containing steam and hydrocarbons by at least the step of adding a first stream of water to the hydrocarbon feedstock in a tower, said stream of water being pre-heated, prior to admission into said tower, with at least a portion of the steam obtained by removing heat from the exothermal reaction;
b) heating said mixture by indirect heat exchange with at least part of said synthesis gas;
c) reforming said mixture after said heating step b).

Preferably, said first stream of water is pre-heated with steam by indirect heat exchange.

The step a) of contacting the hydrocarbon feedstock with said first stream of water is carried out in a saturating tower and the step b) of indirect heat exchange of said mixture containing steam and hydrocarbons is preferably carried out in a saturating heat exchanger. The term "saturating" denotes that, after passage through such equipment, a stream of hydrocarbons becomes enriched with steam.

Said saturating tower and saturating heat exchanger, as well as a reforming section wherein step c) is carried out, are comprised in a front-end section.

The exothermal reaction of the synthesis gas in the presence of catalyst is instead carried out in a synthesis section.

Preferably, said saturating heat exchanger is of the shell-and-tube type. Said second mixture preferably flows in the tube-side with a falling-film flow and the synthesis gas flows in the shell-side. The synthesis gas preferably enters the saturating heat exchanger at a temperature of below 400° C.

According to a preferred embodiment, the formation of said mixture containing steam and hydrocarbons during step a) further comprises the step of mixing the effluent of said saturating tower with a second stream of water, said second stream of water being preferably pre-heated with said synthesis gas.

Preferably, the synthesis gas used for pre-heating said second stream of water is the effluent of said step b) of heating the mixture containing water and hydrocarbons. Said pre-heating takes place in a suitable pre-heater. Accordingly, the synthesis gas traverses in series the saturating heat exchanger, transferring heat to said mixture containing steam and hydrocarbons, and the pre-heater, transferring heat to said second stream of water.

In a preferred embodiment, said second stream of water contains a process condensate stream.

According to a preferred embodiment, excess water is drawn off from the saturating tower. Advantageously, said excess water is partially recirculated in the process and partially directed to a waste water treatment.

Preferably, at least a portion of the excess water recirculated to the process is used to form at least part of said second stream of water. Preferably, said second stream of water is obtained by mixing said excess water with said process condensate stream.

Preferably, at least a portion of said excess water is recirculated inside the saturating tower to contact the hydrocarbon feedstock. Preferably, said portion is heated with part of the exported steam prior to be recirculated inside the saturating tower.

Preferably, a stream of excess water is also drawn off from the step b), i.e. it is drawn off from said saturating heat-exchanger, and is advantageously supplied to the saturating tower, wherein it contacts the hydrocarbon feedstock.

Hence, the input stream of water to the saturating tower may contain, besides the above mentioned first stream of water, at least part of the excess water withdrawn from the saturating tower, which is advantageously pre-heated with steam exported from the reaction step, and/or at least part of the excess water withdrawn from the saturating heat exchanger.

According to a preferred embodiment, the synthesis product obtained with the process according to the invention is methanol. In this case, the first stream of water contacting the hydrocarbon feedstock preferably comprises the bottom water of the distillation section of a methanol plant. According to another preferred embodiment, said synthesis product is ammonia.

The following description will refer to the non-limiting example of a methanol synthesis process.

According to the invention, the saturating tower preferably provides about 45% of the total steam required by the front-end section. In other words, about 45% of the duty necessary for generating the required steam is provided by the synthesis section.

About 50% of the total duty is instead provided by the synthesis gas. This means that the heat recovered in the saturating heat exchanger and the pre-heater supplies about 50% of the total steam required by the front-end section.

The balance, i.e. around 5%, of the process steam is supplied directly to the feedstock of the reforming section.

Accordingly, most steam required by the front-end section is produced inside the front-end section itself, reducing the steam supply from the synthesis section.

The synthesis gas provided by the front-end section of a methanol plant has advantageously a molar ratio ($H_2$—$CO_2$)/($CO+CO_2$) close to 2 and is pressurized to the synthesis pressure of about 80-150 bar before being subjected to the synthesis section.

Preferably, the step of reacting the synthesis gas in the synthesis section comprises at least one isothermal reactive step, providing a methanol-containing stream. Said isothermal reactive step is carried out in a catalyst bed wherein a number of heat exchange bodies immersed therein are traversed by a suitable cooling medium to remove heat generated by the exothermic reaction and keep the reaction temperature within an optimal range. Because the reaction temperature is kept within a narrow range by the cooling effect, the reaction is termed isothermal.

In an embodiment, said cooling medium is boiling water so that the heat removed from the reaction generates steam. At least a portion of said steam can be used to pre-heat the first stream of water entering the saturating tower.

A water-cooled isothermal converter therefore can act as a steam generator or boiler and the cooling water can also be termed boiler feed water (BFW).

According to a preferred embodiment, the so obtained methanol-containing stream is subjected to a further isothermal reactive step, which provides a methanol product. In this case, a stream of synthesis gas may be used as cooling medium to keep the temperature within an optimal range, thus providing a pre-heated stream. Preferably said cooling synthesis gas is fresh (i.e. unreacted) synthesis gas.

The isothermal step wherein boiler feed water is used as cooling medium will be also referred to as first isothermal reactive step. The isothermal step wherein synthesis gas (e.g. fresh synthesis gas) is used as cooling medium will be also referred to as second isothermal reactive step.

Preferably, the feed stream to the first isothermal reactive step comprises said pre-heated stream.

Preferably, the methanol-containing stream obtained from said first isothermal reactive step is quenched with a further portion of the synthesis gas providing a quenched stream, which is further reacted in the second isothermal reactive step.

According to a preferred embodiment of the invention, an input stream of synthesis gas supplying the synthesis section is split into three portions.

In particular, a first and main portion is used as cooling medium in the second isothermal reactive step, thus providing a stream of preheated synthesis gas, a second portion is used for quenching the effluent of the first isothermal reactive step, and a third portion is fed directly to the first isothermal reactive step. Said third portion is advantageously mixed with said stream of preheated synthesis gas to form the feed stream to the first isothermal reactive step.

The term "directly" is used to indicate that said third portion of the input stream is not subjected to thermal exchange and is maintained at a substantially constant temperature.

According to an embodiment of the invention, said input stream of synthesis gas is obtained by pre-heating at least a portion of the effluent of the front-end section. Preferably, said at least a portion is pre-heated in a suitable pre-heater exchanger by indirect heat exchange with the methanol product provided by the second isothermal reactive step.

Further objects of the present invention are a plant and a method of revamping according to the claims.

The present invention has the following advantages.

A first advantage is that the duty necessary for generating the steam required in the front-end section is mainly supplied by the synthesis gas, thus making the front-end section less dependent on the synthesis section.

A further advantage is that the operating parameter of process steam superheaters commonly used to super-heat the steam generated by waste heat boilers downstream of the reforming section can be relaxed. This is because part of the duty of the synthesis gas is given back to the process instead of being used to raise steam. For example, the inlet operating temperature can be decreased from 525° C. to 490° C. with a beneficial effect on the design of such critical equipment.

With particular reference to a methanol plant, another advantage is that the bottom water coming from the distillation section and the process condensate can be treated in the saturating tower and the saturating heat exchanger, respectively, thus eliminating the need of the process condensate stripping section and also greatly reducing the plant liquid effluents. According to the process of the invention, the only effluent is indeed the saturating tower blow down that consists in about 1 kg of water per tonne of methanol sent to a waste water treatment.

Still with reference to a methanol plant, other advantages are related to the embodiment wherein the step of reacting the synthesis gas in the synthesis section further comprises a second isothermal reactive step wherein synthesis gas is used as cooling medium. This embodiment allows to generate less steam in the synthesis section and, at the same time, to reduce the size of the synthesis gas pre-heaters, which are critical equipment.

The advantages of the invention will emerge even more clearly with the aid of the detailed description below relating to preferred embodiments.

DETAILED DESCRIPTION

Figure 1:
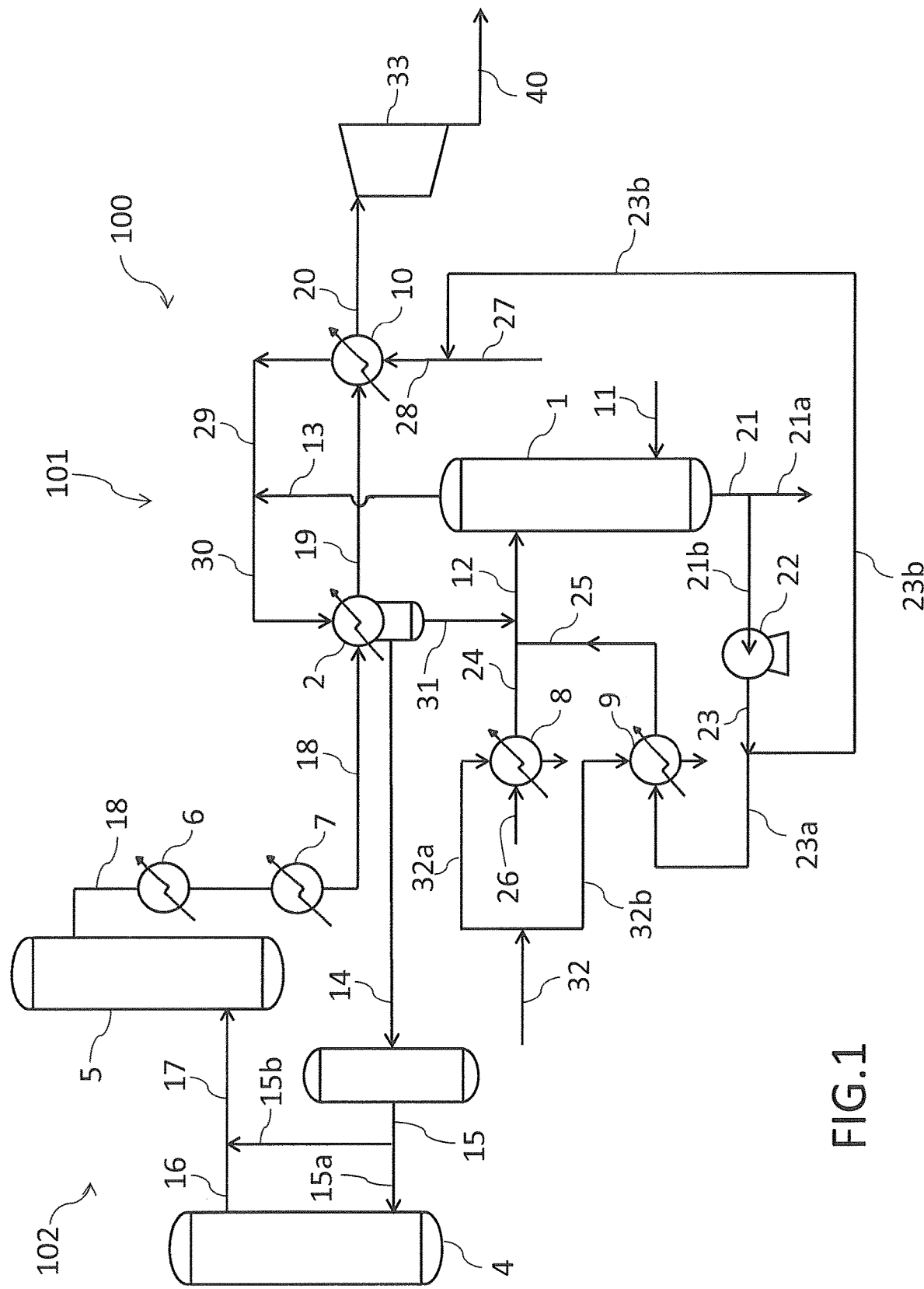
FIG. 1 shows the front-end section of a plant for the synthesis of methanol, according to an embodiment of the invention.

According to FIG. 1, the front-end section 100 of a methanol plant basically comprises a saturating section 101 and a reforming section 102. The saturating section 101 essentially comprises a saturating tower 1 and a saturating heat exchanger 2. The reforming section 102 essentially comprises a pre-reformer 3, a primary steam reformer 4 and a secondary reformer 5, which is for example an autothermal reformer (ATR). According to the example of the figure, the front-end section 100 also comprises a boiler 6 and a steam super-heater 7, which are located in series downstream of the secondary reformer 5.

Said saturating section 101 also comprises a first heat exchanger 8 and a second heat exchanger 9, wherein water is heated by steam recovered from the synthesis section of the plant (shown in FIG. 2) to form at least part of the input stream to the saturating tower 1.

According to the example shown in FIG. 1, the saturating section 101 further comprises a pre-heater 10 as will be better explained below.

The operation of the plant is substantially the following.

A stream 10 of natural gas is supplied to the front-end section 1, wherein contacts a first stream of hot water fed to said saturating tower 1 via line 12, providing an output stream 13 containing steam and natural gas, which furnishes around 45% of the total steam required in the downstream reforming section 102.

Said output stream 13 mixes with a second stream of hot water 29 and the resulting mixture 30 enters the saturating heat exchanger 2, providing the input stream 14 of the reforming section 102. Said input stream 14 has preferably a steam-to-carbon (SC) ratio comprised between 1.8 and 2.8.

The saturating heat exchanger 2 is preferably of the shell-and-tube type, with said mixture 30 flowing in the tube-side thereof with a falling-film flow.

The saturating heat exchanger 2 provides around 50% of the total steam required in the reforming section 102. The balance of the process steam (i.e. around 5%) is supplied directly to the input stream 14 of the reforming section 102 (not shown).

More in detail, the stream 14 is supplied to the pre-reformer 3, wherein reacts to provide an effluent 15. Said effluent 15 splits into a first portion 15a and a second portion 15b. Said first portion 15a is supplied to the primary steam reformer 4, providing a partially reformed gas 16. Said second portion 15b bypasses the primary steam reformer 4 and mixes with the partially reformed gas 16 forming the input stream 17 of the secondary reformer 5, wherein it further reacts providing a reformed gas 18.

According to the example of the figure, said reformed gas 18 passes through the above mentioned boiler 6 and subsequently through the steam super-heater 7.

The reformed gas 18 is supplied to the shell-side of the saturating heat exchanger 2, wherein it acts as heating medium to evaporate at least part of the water contained in the tube-side circulating mixture 30, ultimately providing said input stream 14.

Accordingly, said saturating heat exchanger 2 discharges a cooled stream 19 of reformed gas which enters the pre-heater 10, wherein it acts as heating medium for a water stream 28, providing the second stream of hot water 29 and a reformed gas 20 with lower temperature.

Said second stream of water 29 mixes with the output stream 13 of the saturating tower 1 to form the above mixture 30.

Said reformed gas 20 has advantageously a molar ratio $(H_2-CO_2)/(CO+CO_2)$ close to 2, and is pressurized to about 80-150 bar in a suitable gas compressor 33, thus providing synthesis gas 40 directed to the following synthesis section of the plant (FIG. 2), which produces methanol 47. Within the synthesis section, heat of reaction is removed by producing steam 32, at least a portion of which is recycled back to the front-end section 100, in particular to act as heating medium in the first and second heat exchangers 8, 9.

An excess of water is drawn off from the bottom of the saturating tower 1 via line 21 and splits into a first portion 21a and a second portion 21b. Said first portion 21a is exported from the front-end section 1 and sent to a waste water treatment section (not shown), while said second portion 21b is recirculated into the front-end section 100 through a pump 22 furnishing a pressurized stream 23.

According to the example of FIG. 1, the first stream of hot water feeding the saturating tower 1 via line 12 is obtained by mixing together a first and a second stream of water 24, 25.

Figure 2:
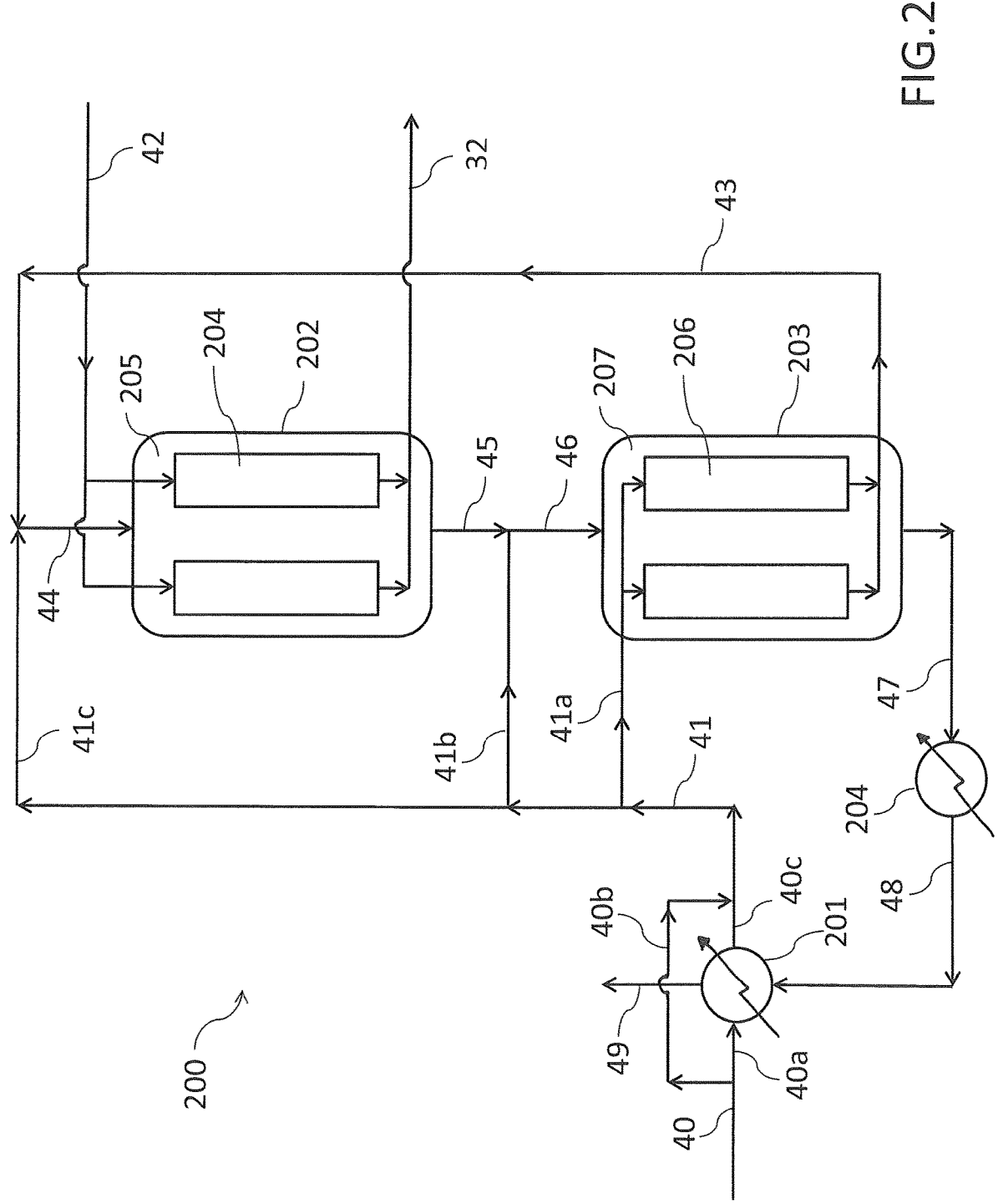
FIG. 2 shows the synthesis section of a plant for the synthesis of methanol according to an embodiment of the invention.

Said first stream 24 is obtained by heating the effluent 26 of a distillation section (not shown) of the plant in the heat-exchanger 8 by means of a portion 32a of steam recovered from the synthesis section of the plant (shown in FIG. 2). Similarly, said second stream 25 is obtained by heating a portion 23a of the above mentioned pressurized stream 23 in the heat-exchanger 9 by means of a portion 32b of said steam.

A further portion 23b of the pressurized stream 23 mixes with a process condensate 27, providing the water stream 28 entering the pre-heater 10.

An excess of water 31 is also withdrawn from said saturating heat exchanger 2 and mixes with the first and second streams 24, 25 to form the input stream 12 feeding the saturating tower 1.

FIG. 2 shows the synthesis section 200 of a methanol plant, wherein an input stream 40 of synthesis gas is converted into methanol. The synthesis section 200 essentially comprises a heat exchanger 201, a first isothermal reactor 202 and a second isothermal reactor 203. Said first and second isothermal reactors 202, 203 are located in series.

A first portion 40a of said input stream 40 of synthesis gas is heated in the heat exchanger 201 by heat-exchange with a methanol-containing stream 48 providing a pre-heated stream 40c, while a second portion 40b bypasses the heat exchanger 201 and merges with said pre-heated portion 40c forming a stream 41 of synthesis gas.

Said stream 41 splits into three portions, namely a first portion 41a, a second portion 41b and a third portion 41c. Said portions 41a-41c have the same composition, but may have different molar flows.

The first isothermal reactor 202 contains heat exchange plates 204 immersed in the catalytic bed 205 and traversed by a stream 42 of boiler feed water, which removes the heat generated in said catalytic bed 205. The water leaves the heat exchange plates 204 as steam 32 which is recycled back to the front-end section 100.

The second isothermal reactor 203 contains heat exchange plates 206 immersed in the catalytic bed 207 and traversed by said first portion 41a of synthesis gas which acts as cooling medium, thus generating a preheated stream 43 of reformed gas.

The third portion 41c of reformed gas is mixed with said preheated stream 43 to form the input stream 44 to the first isothermal reactor 202, wherein it partially reacts providing an output stream 45 containing methanol and unreacted gas.

Said output stream 45 is subsequently mixed with the second portion 41b of synthesis gas to form the input stream 46 to the second isothermal reactor 203, wherein the synthesis gas is further converted providing a methanol-containing product stream 47.

Said product stream 47 is pre-cooled in a boiler feed water pre-heater 204 to form the stream 48 which is used as heating medium in the heat exchanger 201. A methanol-containing stream 49 with decreased temperature leaves the heat exchanger 201 and is subjected to purification in a suitable purification section (not shown).

The presence of said heat exchanger 201 is advantageous because allows to modulate the temperatures of the portions 41a, 41b, 41c of reformed gas.

The invention claimed is:

1. A synthesis process, comprising:
   steam reforming a gaseous hydrocarbon feedstock, thereby obtaining a synthesis gas;
   exothermically reacting said synthesis gas in the presence of a catalyst, thereby obtaining a synthesis product;
   removing heat from said exothermal reaction by producing steam, wherein at least part of said steam provides a heat input to the reforming of said hydrocarbon feedstock;
   wherein the steam reforming of the hydrocarbon feedstock includes:
   a) forming a mixture containing steam and hydrocarbons by at least a step of adding a first stream of water to the hydrocarbon feedstock in a saturating tower, said stream of water being pre-heated by indirect heat exchange, prior to admission into said tower, with at least a portion of the steam produced by removing heat from the exothermal synthesis reaction;
   b) heating said mixture by indirect heat exchange with at least part of said synthesis gas; and
   c) reforming said mixture after said heating step b).

2. The synthesis process of claim 1, wherein the formation of said mixture further includes mixing an effluent of said tower with a second stream of water, and said second stream is pre-heated by indirect heat exchange with said synthesis gas.

3. The synthesis process of claim 2, wherein a stream of synthesis gas transfers heat to said mixture during the heating step b), and the synthesis gas effluent of said heating step b) transfers heat to said second stream of water.

4. The synthesis process of claim 1, wherein excess water is drawn off from the saturating tower during said step a) and at least a portion of said excess water is recirculated into the tower, said portion being pre-heated, prior to admission into said tower, with a portion of the steam produced by removing heat from the exothermal synthesis reaction.

5. The synthesis process of claim 2, wherein excess water is drawn off from the tower during said step a) and said second stream of water includes a portion of said excess water.

6. The synthesis process of claim 1, wherein excess water is drawn off from the step b) and at least a portion of said excess water is added to the hydrocarbon feedstock in said saturating tower.

7. The synthesis process of claim 1, wherein said synthesis product includes methanol.

8. The synthesis process of claim 7, wherein the step of reacting the synthesis gas includes an isothermal reactive step, providing a methanol-containing stream, and wherein a stream of boiling water acts as cooling medium that removes heat of the exothermic reaction of the synthesis gas and generates said steam.

9. The synthesis process of claim 8, wherein said step of reacting the synthesis gas further includes subjecting said methanol-containing stream to a further isothermal reactive step, providing said methanol product, and wherein a stream of fresh synthesis gas acts as cooling medium.

* * * * *